(12) United States Patent
Kamimura

(10) Patent No.: US 10,335,067 B2
(45) Date of Patent: Jul. 2, 2019

(54) OPTICAL UNIT AND OPTICAL ANALYSIS DEVICE

(71) Applicant: NEC Solution Innovators, Ltd., Tokyo (JP)

(72) Inventor: Ippei Kamimura, Tokyo (JP)

(73) Assignee: NEC SOLUTION INNOVATORS, LTD., Tokyo (JP)

(*) Notice: Subject to any disclaimer, the term of this patent is extended or adjusted under 35 U.S.C. 154(b) by 790 days.

(21) Appl. No.: 14/897,412

(22) PCT Filed: May 22, 2014

(86) PCT No.: PCT/JP2014/063528
§ 371 (c)(1),
(2) Date: Dec. 10, 2015

(87) PCT Pub. No.: WO2014/199792
PCT Pub. Date: Dec. 18, 2014

(65) Prior Publication Data
US 2016/0143565 A1 May 26, 2016

(30) Foreign Application Priority Data

Jun. 11, 2013 (JP) ................................ 2013-122434

(51) Int. Cl.
*A61B 5/1455* (2006.01)
*G01N 21/49* (2006.01)
(Continued)

(52) U.S. Cl.
CPC .......... *A61B 5/1455* (2013.01); *A61B 5/1451* (2013.01); *A61B 5/14532* (2013.01);
(Continued)

(58) Field of Classification Search
None
See application file for complete search history.

(56) References Cited

U.S. PATENT DOCUMENTS 5,556,529 A 9/1996 Nemoto
2008/0060148 A1* 3/2008 Pinyayev ............ A61B 5/0088
15/22.1
(Continued)

FOREIGN PATENT DOCUMENTS

EP 0724153 A1 7/1996
JP H02-059914 A 2/1990
(Continued)

OTHER PUBLICATIONS

Chinese Office Action issued by the State Intellectual Property Office of the People's Republic of China for Chinese Application No. 201480033414.2 dated Mar. 31, 2017 (23 pages).
(Continued)

*Primary Examiner* — Eric F Winakur
*Assistant Examiner* — Marjan Fardanesh
(74) *Attorney, Agent, or Firm* — Wilmer Cutler Pickering Hale and Dorr LLP

(57) ABSTRACT

An optical unit (100) includes a light-emitting portion (10) that irradiates an analysis target with light, light-receiving portions (20) that receive light that has been reflected or diffused by the analysis target, a mounting substrate (30) on which these portions are mounted, and a plate-shaped member (40) having optical transparency. The plate-shaped member (40) is arranged so as to cover the light-emitting portion (10) and the light-receiving portions (20) that are mounted on the mounting substrate (30). Positions of the light-emitting portion (10), the light-receiving portions (20), and the plate-shaped member (40) are set such that, in the case where the analysis target is in contact with the plate-shaped member (40), light emitted from the light-emitting portion (10) is incident on two or more of the light-receiving portions (20) after being reflected or diffused by the analysis target.

16 Claims, 10 Drawing Sheets

(51) Int. Cl.
*A61B 5/145* (2006.01)
*G01N 21/31* (2006.01)

(52) U.S. Cl.
CPC ......... *A61B 5/14546* (2013.01); *G01N 21/49* (2013.01); *A61B 2562/0238* (2013.01); *G01N 2021/3181* (2013.01); *G01N 2201/0627* (2013.01)

(56) References Cited

U.S. PATENT DOCUMENTS

| 2008/0097172 A1* | 4/2008 | Sawada | A61B 5/0261 600/310 |
| 2008/0103396 A1* | 5/2008 | Johnson | A61B 5/0071 600/477 |
| 2008/0183056 A1 | 7/2008 | Atsumori et al. | |
| 2013/0022363 A1 | 1/2013 | Naka et al. | |

FOREIGN PATENT DOCUMENTS

| JP | H0829326 A | 2/1996 |
| JP | H11-244266 A | 9/1999 |
| JP | 2000-503122 A | 3/2000 |
| JP | 2001-326382 A | 11/2001 |
| JP | 3396222 B2 | 4/2003 |
| JP | 2006-230657 A | 9/2006 |
| JP | 2009-011753 A | 1/2009 |
| JP | 2009-106376 A | 5/2009 |
| JP | 4470939 B2 | 6/2010 |
| JP | 2011-064596 A | 3/2011 |
| JP | 2012-217570 A | 11/2012 |
| JP | 2013-024752 A | 2/2013 |
| WO | WO-95/12349 A1 | 5/1995 |
| WO | WO-1997/025613 A1 | 7/1997 |
| WO | WO-99/40842 A1 | 8/1999 |
| WO | WO-2013/056379 A1 | 4/2013 |

OTHER PUBLICATIONS

Extended European Search Report issued in corresponding European Patent Application No. 14810597.6, dated Jan. 13, 2017, 9 pages.
International Search Report corresponding to PCT/JP2014/063528 dated Jul. 15, 2014 (2 pages).
Partial Supplementary European Search Report issued in corresponding European Patent Application No. 14810597.6, dated Oct. 25, 2016, 8 pages.

* cited by examiner

OPTICAL UNIT AND OPTICAL ANALYSIS DEVICE

CROSS-REFERENCE TO RELATED APPLICATIONS

This application is a national stage application of International Application No. PCT/JP2014/063528 entitled "Optical Unit and Optical Analysis Device" filed on May 22, 2014, which claims priority to Japanese Application No. 2013-122434 filed on Jun. 11, 2013, the disclosures of which are hereby incorporated by reference in their entirety.

TECHNICAL FIELD

The present invention relates to an optical unit to be used for optical analysis and an optical analysis device including the optical unit.

BACKGROUND ART

In recent years, in the field of component analysis, optical analysis has also been carried out, in addition to analysis using chemical reactions. For example, Patent Documents 1 to 4 disclose conventional optical analysis devices for carrying out optical analysis. Also, in optical analysis, a sample is irradiated with unpolarized near-infrared light, and reflected light that was reflected by the sample or transmitted light that was transmitted by the sample is received by a light-receiving element, for example. The components in the sample are then specified based on the wavelength, intensity, and the like of received light.

In particular, Patent Document 1 discloses a blood glucose meter that measures a blood glucose level in the blood through optical analysis. The blood glucose meter disclosed in Patent Document 1 includes an optical unit configured by a light-emitting diode and a photodiode. Moreover, the blood glucose meter disclosed in Patent Document 1 is provided in a state in which blood, which is a sample, adheres to a discoidal measurement chip.

Because this measurement chip includes test paper that reacts with glucose in the blood and changes color, the blood glucose level is measured by irradiating the measurement chip with light having a specific wavelength that is emitted from the light-emitting diode, receiving light reflected by the test paper using the photodiode, and determining the intensity of the reflected light.

LIST OF PRIOR ART DOCUMENTS

Patent Document

Patent Document 1: JP 2011-64596A
Patent Document 2: JP H02-059914A
Patent Document 3: JP 2001-326382A
Patent Document 4: JP 2009-011753A

DISCLOSURE OF THE INVENTION

Problems to be Solved by the Invention

With the blood glucose meter disclosed in Patent Document 1, a specific area of the measurement chip needs to be reliably irradiated with light emitted from the light-emitting diode, and therefore it is necessary to secure the length of a light path to some extent (10 mm or more) from an emission surface of the light-emitting diode to the irradiation surface of the measurement chip so that luminous flux sufficiently spreads. Moreover, in order to efficiently reflect emitted light, it is preferable that the incidence angle and reflection angle of light on the irradiation surface are about 45 degrees, and thus if the length of the light path is long, it is also necessary for the distance between the light-emitting diode and the photodiode to be long. Accordingly, there is a problem with the blood glucose meter disclosed in Patent Document 1 in that it is difficult to make the optical unit smaller and the device cannot be reduced in size.

An object of the present invention is to resolve the above-described problems and to provide an optical unit and an optical analysis device that enable a reduction in the size of the optical analysis device to be achieved.

Means for Solving the Problems

In order to achieve the above-described object, an optical unit according to an aspect of the present invention includes:
a light-emitting portion that irradiates an analysis target with light;
a plurality of light-receiving portions that receive light that has been reflected or diffused by the analysis target;
a mounting substrate on which the light-emitting portion and the plurality of light-receiving portions are mounted; and
a plate-shaped member having optical transparency,
wherein the plate-shaped member is arranged so as to cover the light-emitting portion and the plurality of light-receiving portions that are mounted on the mounting substrate, and
positions of the light-emitting portion, the light-receiving portions, and the plate-shaped member are respectively set such that, in a case where the analysis target is in contact with the plate-shaped member, light emitted from the light-emitting portion is incident on two or more of the light-receiving portions after being reflected or diffused by the analysis target.

Also, in order to achieve the above-described object, an optical analysis device according to an aspect of the present invention is a device for analyzing a specific component included in an analysis target, including:
an optical unit including a light-emitting portion that irradiates the analysis target with light, a plurality of light-receiving portions that receive light that has been reflected or diffused by the analysis target, a mounting substrate on which the light-emitting portion and the plurality of light-receiving portions are mounted, and a plate-shaped member having optical transparency,
wherein the plate-shaped member is arranged so as to cover the light-emitting portion and the plurality of light-receiving portions that are mounted on the mounting substrate, and
positions of the light-emitting portion, the light-receiving portions, and the plate-shaped member are respectively set such that, in a case where the analysis target is in contact with the plate-shaped member, light emitted from the light-emitting portion is incident on two or more of the light-receiving portions after being reflected or diffused by the analysis target.

Advantageous Effects of the Invention

As described above, according to the present invention, a reduction in the size of an optical analysis device can be achieved.

MODE FOR CARRYING OUT THE INVENTION

Embodiment 1

Figure 1:
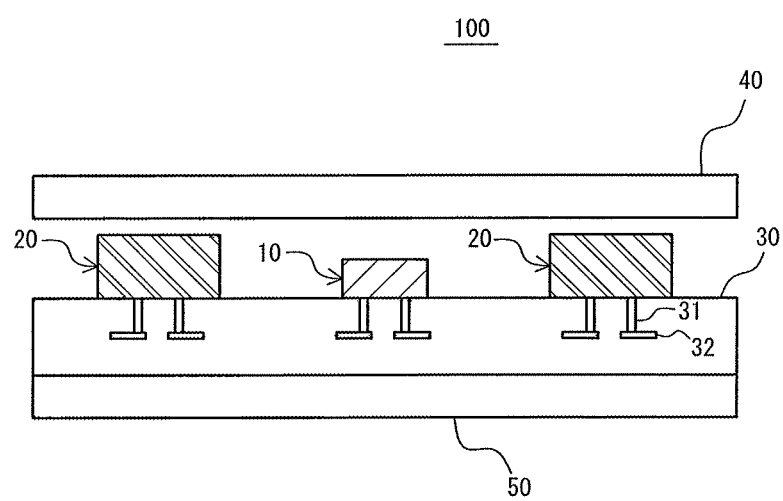
FIG. 1 is a cross-sectional view schematically showing a configuration of an optical unit according to Embodiment 1 of the present invention.
Figure 2:
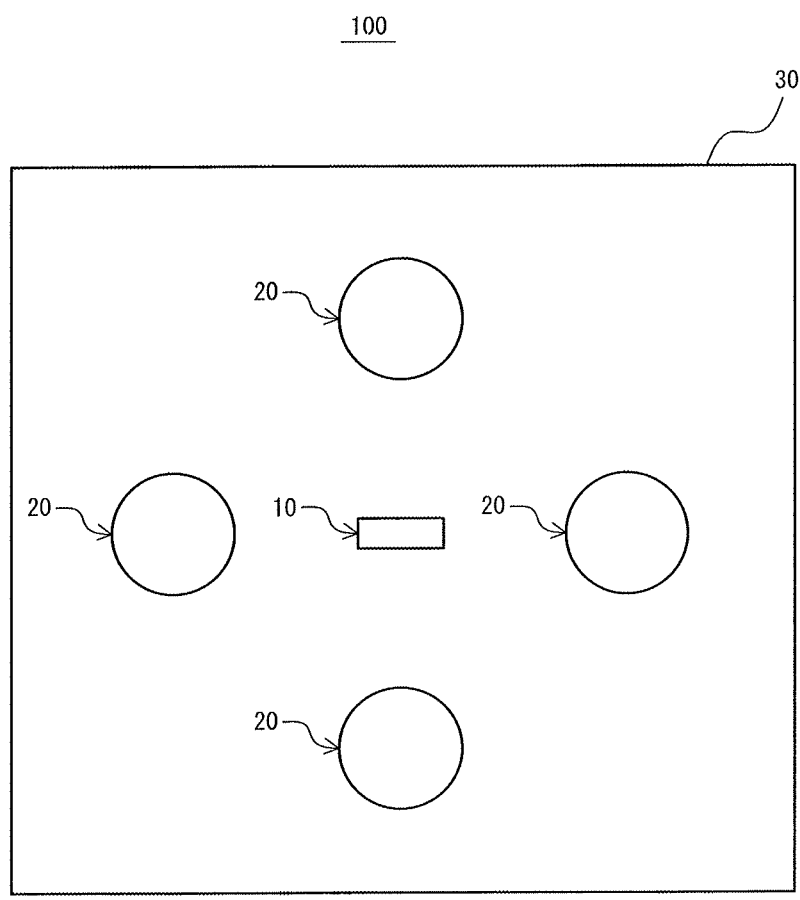
FIG. 2 is a plan view schematically showing a configuration of the optical unit according to Embodiment 1 of the present invention.
Figure 3:
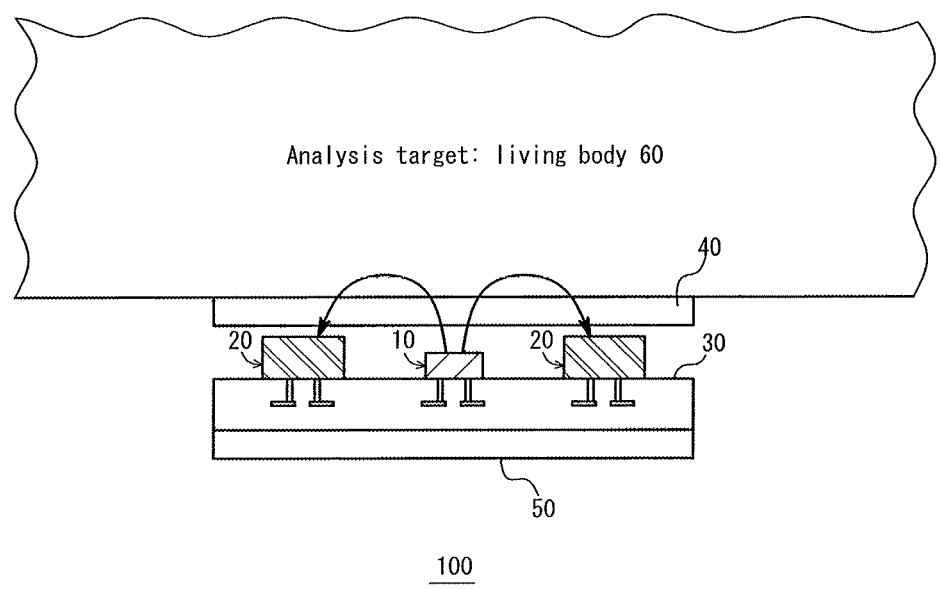
FIG. 3 is a diagram showing the principle of operations of the optical unit shown in FIGS. 1 and 2.

Hereinafter, an optical unit and an optical analysis device according to Embodiment 1 of the present invention will be described with reference to FIGS. 1 and 2.
Optical Unit First, the optical unit according to Embodiment 1 will be described with reference to FIGS. 1 to 3. FIG. 1 is a cross-sectional view schematically showing the configuration of the optical unit according to Embodiment 1 of the present invention. FIG. 2 is a plan view schematically showing the configuration of the optical unit according to Embodiment 1 of the present invention. FIG. 3 is a diagram showing the principle of operations of the optical unit shown in FIGS. 1 and 2.

An optical unit 100 of Embodiment 1 shown in FIGS. 1 to 3 is used for analyzing a specific component included in an analysis target 60 (see FIG. 3). As shown in FIGS. 1 and 2, the optical unit 100 includes a light-emitting portion 10, a plurality of light-receiving portions 20, a mounting substrate 30 on which the light-emitting portion 10 and the light-emitting portions 20 are mounted, and a plate-shaped member 40 having optical transparency. Note that hatching of the mounting substrate 30 and the plate-shaped member 40 is omitted in FIGS. 1 and 3. Also, the plate-shaped member 40 is omitted in FIG. 2.

The mounting substrate 30 is used for mounting the light-emitting portion 10 and the plurality of light-receiving portions 20. Also, the plate-shaped member 40 is arranged so as to cover, the light-emitting portion 10 and the light-receiving portions 20 that are mounted on the mounting substrate 30.

Also, as shown in FIG. 3, in the case where the analysis target 60 is in contact with the plate-shaped member 40, light emitted from the light-emitting portion 10 is reflected or diffused by the analysis target 60 in the optical unit 100. At this time, since the light reflected or diffused by the analysis target 60 spreads horizontally, light is incident on two or more of the light-receiving portions 20. Also, the light-receiving portions 20, upon receiving light, output signals required for analyzing a specific component of the analysis target 60. Note that in FIG. 3, arrows represent light that is diffused by the analysis target 60 after being emitted from the light-emitting portion 10, and is then incident on the light-receiving portions 20.

The positions of the light-emitting portion 10, the light-receiving portions 20, and the plate-shaped member 40 are respectively set such that emission, reflection or diffusion, and incidence of light occur in this manner. In other words, as shown in FIG. 3, by bringing the plate-shaped member 40 close to the light-emitting portion 10 and the light-receiving portions 20, the length of a light path between the light-emitting portion 10 and the analysis target 60 is shortened, and by further bringing the light-receiving portions 20 and the light-emitting portion 10 close to each other, the above-described emission, reflection or diffusion, and incidence of light are established.

Also, as a result of such position settings, in the optical unit 100, the length of the light path between the light-emitting portion 10 and the analysis target 60 is shortened (5 mm or less, for example), and light reflected or diffused by the analysis target 60 is reliably received. Therefore, according to the optical unit 100, a reduction in the size of the unit itself and a reduction in the size of an optical analysis device 200 (see FIG. 4, which will be described later) that uses the optical unit 100 can be achieved.

Furthermore, since light emitted from the light-emitting portion 10 is received by two or more of the light-receiving portions 20, each of the two or more light-receiving portions 20 outputs a signal in accordance with the intensity of the received light. Accordingly, the optical analysis device 200 can execute arithmetic processing, noise removal processing, and the like using two or more signals, and therefore an improvement in analysis accuracy can be achieved. Moreover, since signals are output from two or more of the light-receiving portions, even though the size of each light-receiving portion 20 is reduced, the sensitivity of the light-receiving portions as a whole can be ensured. Therefore, a reduction in the size of the optical unit can also be attained in this regard.

Also, since the optical unit 100 can receive diffused light or reflected light required to analyze components included in the analysis target 60 simply by bringing the analysis target 60 in contact with the plate-shaped member 40, an improvement in the usability of the optical analysis device 200 (see FIG. 4, which will be described later) for the user can also be achieved.

Here, the configuration of the optical unit 100 in Embodiment 1 will be more specifically described. First, in Embodiment 1, the light-emitting portion 10 is configured by a light-emitting element such as a light-emitting diode, and the emission surface of the light-emitting element faces the plate-shaped member 40. The light-receiving portions 20 are configured by a light-receiving element such as a photodiode, and the light-receiving surface thereof faces the plate-shaped member 40.

Also, in Embodiment 1, the analysis target 60 is a living body, and the specific component is glucose included in interstitial fluid or blood of the living body. In this case, examples of the light-emitting element in the light-emitting portion 10 include a light-emitting diode that can emit light in a near-infrared region. Note that in the examples shown in FIGS. 1 to 4, the specific component is glucose included in interstitial fluid, and light diffused by glucose is received by the light-receiving portions 20. Also, in this case, the palm of a hand is used as the living body 60, for example.

Furthermore, in this embodiment, the specific component of the living body may be a component other than glucose, and may be fat, an enzyme, or the like, for example. Moreover, feces and urine, blood, interstitial fluid, or the like collected from a living body may serve as the analysis target 60.

Also, in Embodiment 1, the analysis target 60 is not limited to a living body. Other specific examples of the analysis target 60 include food (agricultural products, aquatic products, meat, various types of processed food, and the like), industrial goods (gasoline, kerosene, heavy oil, light oil, fiber, pharmaceutical products, polymers, paint, and the like), pharmaceutical products, and soil. For example, in the case where the analysis target 60 is an agricultural product such as a fruit or vegetable, examples of the specific component include fructose, in addition to glucose. Also, in the case where the analysis target is meat, examples of the specific component include fat. Furthermore, in the case where the analysis target is a polymer, examples of the specific component include moisture.

Note that in these cases, the wavelength of light emitted from a light-emitting element 11 is set in accordance with the type of specific component. Also, a light-emitting element other than a light-emitting diode may be used as the light-emitting element in the light-emitting portion.

Also, as shown in FIGS. 1 to 3, the optical unit 100 further includes a cooling element 50. The cooling element 50 is arranged so as to be in contact with a surface of the mounting substrate 30 on which the light-emitting portion 10 and the light-receiving portions 20 are not mounted. Specific examples of the cooling element 50 include a Peltier element. According to the cooling element 50, variation in the light quantity of the light-emitting element 11 and a decrease in the accuracy of the light-receiving element are further suppressed. Also, if the analysis target 60 generates heat, the accuracy of the light-receiving element may also decrease due to the heat, but according to the cooling element 50, effects due to the heat of the analysis target 60 can also be suppressed. Note that hatching of the cooling element 50 is also omitted in FIGS. 1 and 3.

Optical Analysis Device

Figure 4:
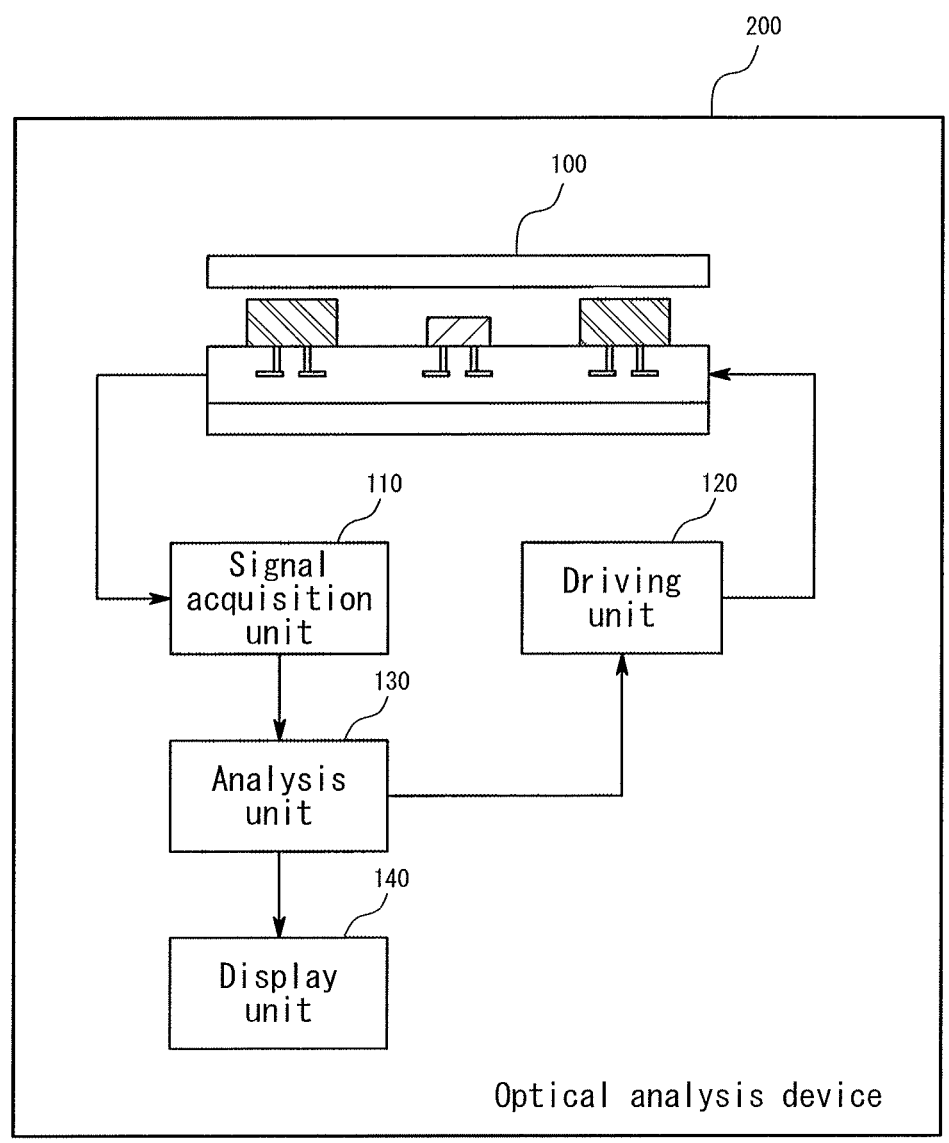
FIG. 4 is a block diagram schematically showing a configuration of an optical analysis device according to Embodiment 1 of the present invention.

Next, an optical analysis device according to Embodiment 1 will be described with reference to FIG. 4. FIG. 4 is a block diagram schematically showing the configuration of the optical analysis device according to Embodiment 1 of the present invention.

As shown in FIG. 4, an optical analysis device 200 is a device that analyzes a specific component included in the analysis target 60, and includes the optical unit 100. The optical unit 100 shown in FIG. 4 is similar to the optical unit shown in FIG. 1.

Also, in addition to the optical unit 100, the optical analysis device 200 includes a signal acquisition unit 110, a driving unit 120, an analysis unit 130, and a display unit 140. Among these portions, the signal acquisition unit 110 acquires signals output in accordance with the intensity of light received by the light-receiving portions 20. Also, since the acquired signals are analog signals, the signal acquisition unit 110 converts the acquired signals into digital signals, and outputs the digital signals obtained by the conversion to the analysis unit 130.

The driving unit 120 causes the light-emitting element of each light-emitting portion 10 to emit light in accordance with an instruction received from the analysis unit 130. Specifically, the driving unit 120 has a power supply circuit, and supplies power to the light-emitting element via the power supply circuit.

The analysis unit 130 calculates absorbance of the analysis target 60 based on the signals output from the signal acquisition unit 110, and further coverts the calculated absorbance into a glucose concentration (blood glucose level). Specifically, the analysis unit 130 calculates absorbance through applying the output value of the signal output from the signal acquisition unit 110 to a preset conversion equation. Furthermore, the analysis unit 130 calculates the glucose concentration through applying the calculated absorbance to a calibration curve defining a relationship between absorbance and glucose concentration.

Also, the display unit 140 is a display device such as a liquid crystal display panel. The analysis unit 130 causes the display unit 140 to display the calculated glucose concentration.

Also, in Embodiment 1, the signal acquisition unit 110, the driving unit 120, and the analysis unit 130 can be realized by an IC (Integrated Circuit) chip. In this case, because the IC chips and the liquid crystal display panel functioning as the display unit 140 can be mounted on the mounting substrate 30 of the optical unit 100, it is possible to facilitate a further reduction in the size of the optical analysis device 200.

Embodiment 2

Next, an optical unit and an optical analysis device according to Embodiment 2 of the present invention will be described with reference to FIGS. 5 to 8.

Optical Unit

Figure 5:
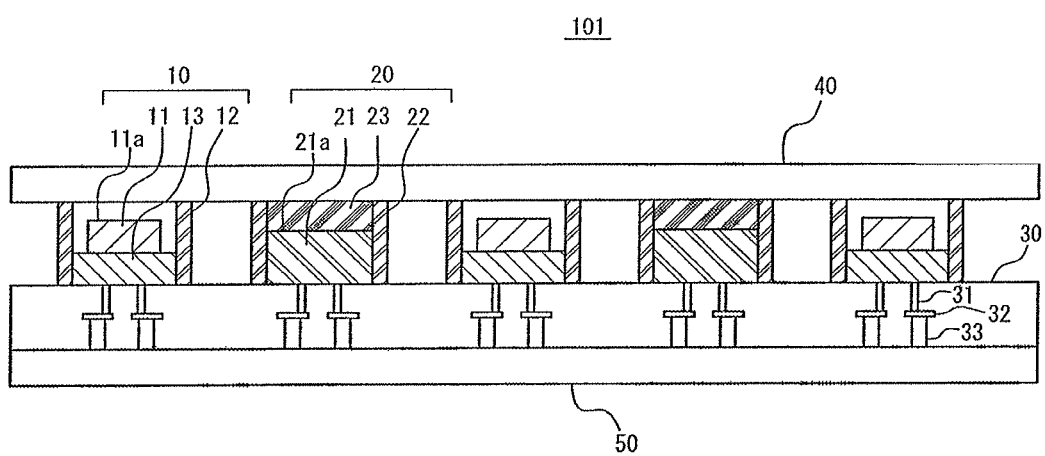
FIG. 5 is a cross-sectional view schematically showing a configuration of an optical unit according to Embodiment 2 of the present invention.
Figure 6:
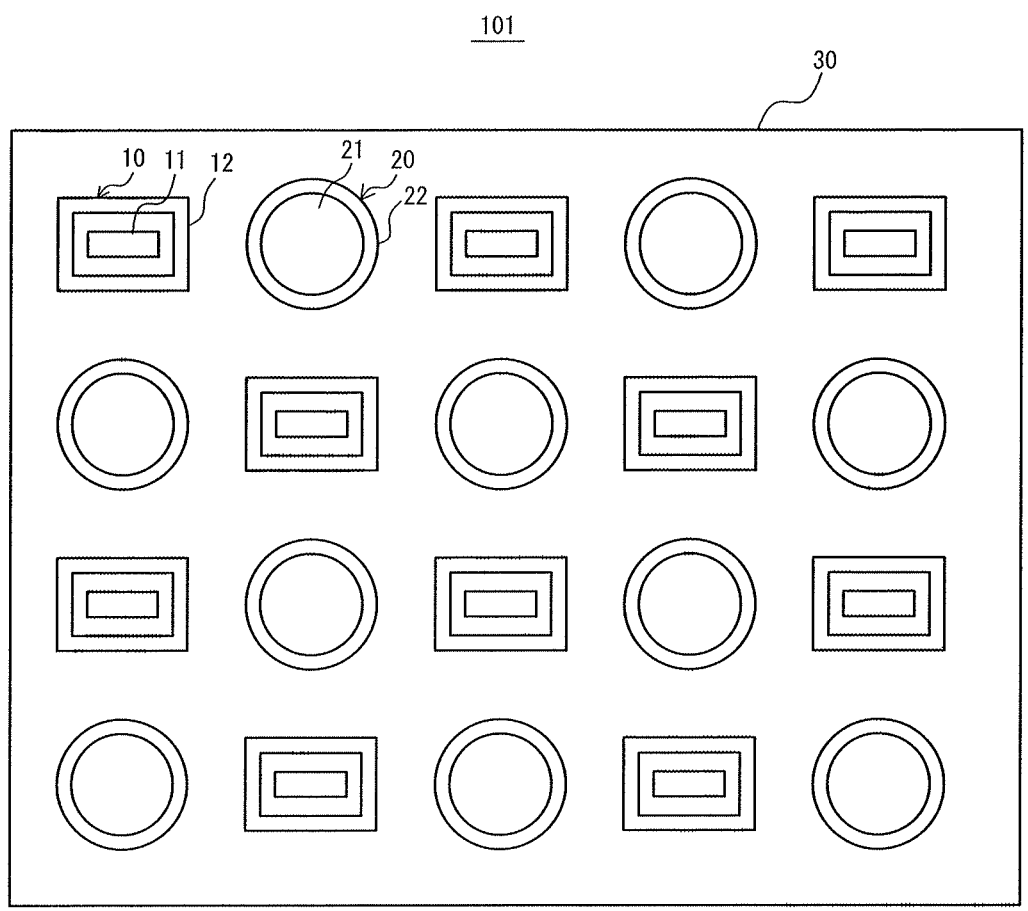
FIG. 6 is a plan view schematically showing the configuration of the optical unit according to Embodiment 2 of the present invention.
Figure 7:
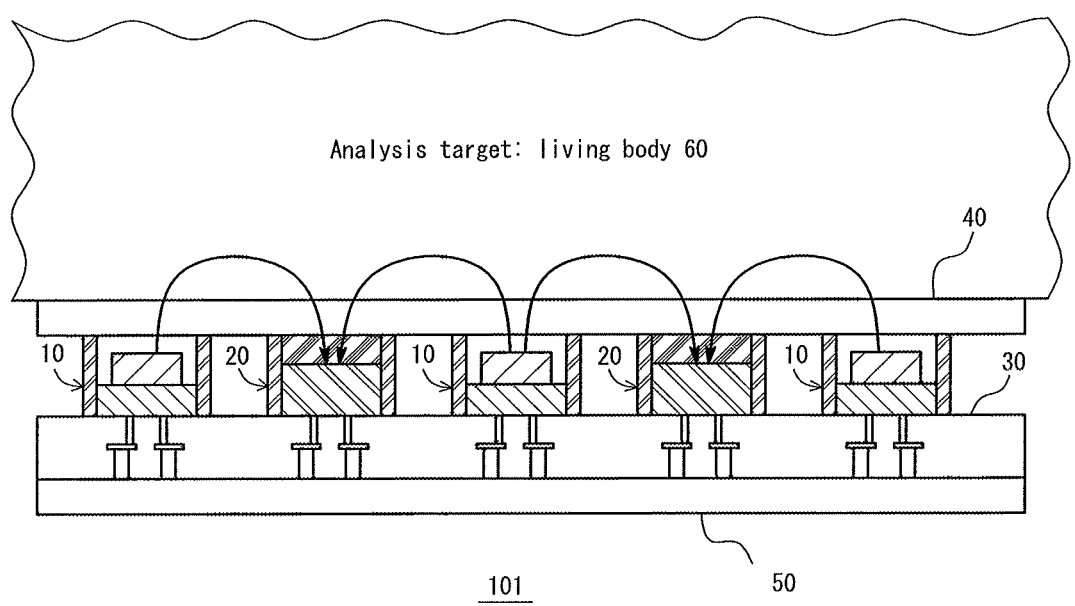
FIG. 7 is a diagram showing the principle of operations of the optical unit shown in FIGS. 5 and 6.

First, the optical unit according to Embodiment 2 will be described with reference to FIGS. 5 to 7. FIG. 5 is a cross-sectional view schematically showing the configuration of the optical unit according to Embodiment 2 of the present invention. FIG. 6 is a plan view schematically showing the configuration of the optical unit according to Embodiment 2 of the present invention. FIG. 7 is a diagram showing the principle of operations of the optical unit shown in FIGS. 5 and 6.

Similarly to the optical unit 100 of Embodiment 1, the optical unit 101 of Embodiment 2 shown in FIGS. 5 to 7 is also used for analyzing a specific component included in an analysis target 60 (see FIG. 7).

However, the optical unit 101 of Embodiment 2 is different from the optical unit 100 of Embodiment 1 in the following points. Hereinafter, Embodiment 2 will be described, focusing on the differences from Embodiment 1. Note that hatching of a mounting substrate 30 and a plate-shaped member 40 is omitted in FIGS. 5 and 7. Also, the plate-shaped member 40 is omitted in FIG. 6.

First, as shown in FIGS. 5 to 7, in Embodiment 2, the optical unit 101 includes a plurality of light-emitting portions 10, and the plurality of light-emitting portions 10 are also mounted on the mounting substrate 30. Also, since there are a plurality of light-emitting portions 10, the number of the light-emitting portions 20 is also greater than that in the case of Embodiment 1.

As shown in FIG. 7, in Embodiment 2, in the case where the analysis target 60 is in contact with the plate-shaped member 40, light emitted from each of the light-emitting portions 10 is incident on two or more of the light-receiving portions 20 adjacent to the light-emitting portion 10 that emitted the light after being reflected or diffused by the analysis target 60. Also, in Embodiment 2 as well, the positions of the light-emitting portions 10, the light-receiving portions 20, and the plate-shaped member 40 are respectively set such that emission, reflection or diffusion, and incidence of light occur in this manner.

Note that in FIG. 7, light emitted from the light-emitting portions 10 located on both sides is reflected or diffused, and then incident on two or more of the light-receiving portions 20 including the light-receiving portions 20 that are not shown (see FIG. 6). Also, similarly to FIG. 3, in FIG. 7 as well, arrows represent light that is diffused by the analysis target 60 after being emitted from the light-emitting portions 10, and is then incident on the light-receiving portions 20.

In this manner, the optical unit 101 of Embodiment 2 includes a plurality of light-emitting portions 10, and light can be emitted and received in a wider range compared to the optical unit 100 of Embodiment 1. Therefore, according to the optical unit 101, it is possible to increase analysis accuracy in an optical analysis device 201 (see FIG. 8) that uses the optical unit 101.

Also, similarly to the optical unit 100 of Embodiment 1, in the optical unit 101 as well, it is possible to shorten the length of a light path between the light-emitting portion 10 and the analysis target 60 (5 mm or less, for example), and to reliably receive light reflected or diffused by the analysis target 60. Accordingly, in Embodiment 2 as well, a reduction in the size of the optical unit 101 and the size of the optical analysis device 201 (see FIG. 8, which will be described later) that uses the optical unit 101 can be achieved.

Also, as shown in FIG. 5, in Embodiment 2, each light-emitting portion 10 includes a light-emitting element 11 arranged so that an emission surface 11a faces the plate-shaped member 40, and a light-blocking wall 12 provided so as to surround the emission surface 11a. Furthermore, the light-receiving portions 20 each includes a light-receiving element 21 arranged so that a light-receiving surface 21a faces the plate-shaped member 40, and a light-blocking wall 22 provided so as to surround the light-receiving surface 21a.

Since such a light-blocking wall 12 and light-blocking wall 22 are provided, it is possible to prescribe the directions of emitted light and incident light, and to avoid a situation in which light emitted from the light-emitting portion 10 is directly incident on the light-receiving portion 20. Also, in particular, on the light-receiving side, it is possible to inhibit light that passes through the analysis target 60 from the outside, noise specific to the analysis target 60 (noise deriving from blood vessels of the living body, for example), or the like from being incident on the light-receiving portions 20. As a result, it is possible to increase analysis accuracy in the optical analysis device 201 (see FIG. 8) that uses the optical unit 101.

Furthermore, as shown in FIGS. 5 and 7, it is preferable that the height of each of the light-blocking walls 12 of the light-emitting portions 10 and the light-blocking walls 22 of the light-receiving portions 20 is set so as to match the distance between the plate-shaped member 40 and the mounting substrate 30. This is for further increasing the above-described effects.

Note that there is no particular limitation on the material for forming the light-blocking wall 12 and the light-blocking wall 22 as long as the material can block light. Also, examples of the light-emitting element 11 and the light-receiving element 21 include the light-emitting diode and the photodiode that are described in Embodiment 1.

Also, in Embodiment 2, each light-receiving portion 20 also includes an optical filter 23 that transmits only light having a set wavelength or less (or more) on the incident side of the light-receiving surface 21a. It is also possible to increase analysis accuracy in the optical analysis device 201 (see FIG. 8) that uses the optical unit 101 in this regard. Note that the set wavelength of the optical filter 23 is set in accordance with the type of specific component.

Furthermore, although the light-blocking wall is formed for each light-emitting portion 10 and light-receiving portion 20 in the example of FIGS. 5 to 7, Embodiment 2 is not limited to this, and a mode may be used in which all of the light-blocking walls are formed integrally. Also, it is preferable that a reflection film is formed on the inner side of each light-blocking wall using a metallic material.

Also, as shown in FIGS. 5 and 7, the light-emitting portions 10 each includes, between the light-emitting element 11 and the mounting substrate 30, a heat transmission member 13 for transmitting heat generated in the light-emitting element 11 to the mounting substrate 30. Examples of the material for forming this heat transmission member 13 include a material having high thermal conductivity, such as marble or a ceramic. Variation in the light quantity of the light-emitting element (light-emitting diode) 11 due to heat can be suppressed by such a heat transmission member 13. Also, since the heat from the light-emitting element 11 is unlikely to be transmitted to the light-receiving element 21, a decrease in the accuracy of the light-receiving element due to heat can also be suppressed. Thus, analysis accuracy in the optical analysis device 201 (see FIG. 8) that uses the optical unit 101 can also be increased by the heat transmission member 13.

In addition, in Embodiment 2, in the light-emitting portion 10, it is also possible to fill an optically transparent resin between the light-emitting element 11 and the light-blocking wall 12, and to form this resin into a lens. In this case, it is possible to increase the efficiency of light with which the analysis target 60 is irradiated.

Also, as shown in FIGS. 5 and 7, similarly to Embodiment 1, the optical unit 101 further includes a cooling element 50 in Embodiment 2 as well. Note that hatching of the cooling element 50 is also omitted in FIGS. 5 and 7.

Also, a conduction channel 31 and wiring 32 that are connected to terminals (not shown) of the light-emitting element 11 and the light-receiving element 21 are formed on the mounting substrate 30, and a heat conduction channel 33 that connects the wiring 32 and the cooling element 50 is further provided in Embodiment 2. Therefore, heat generated in the light-emitting element 11 and the light-receiving element 21 is efficiently discharged to the cooling element 50 via the conduction channel 31, the wiring 32, and the heat conduction channel 33. Note that there is no particular limitation on the material for forming the conduction channel 31, the wiring 32, and the heat conduction channel 33 as long as the material is a metallic material.

Optical Analysis Device

Figure 8:
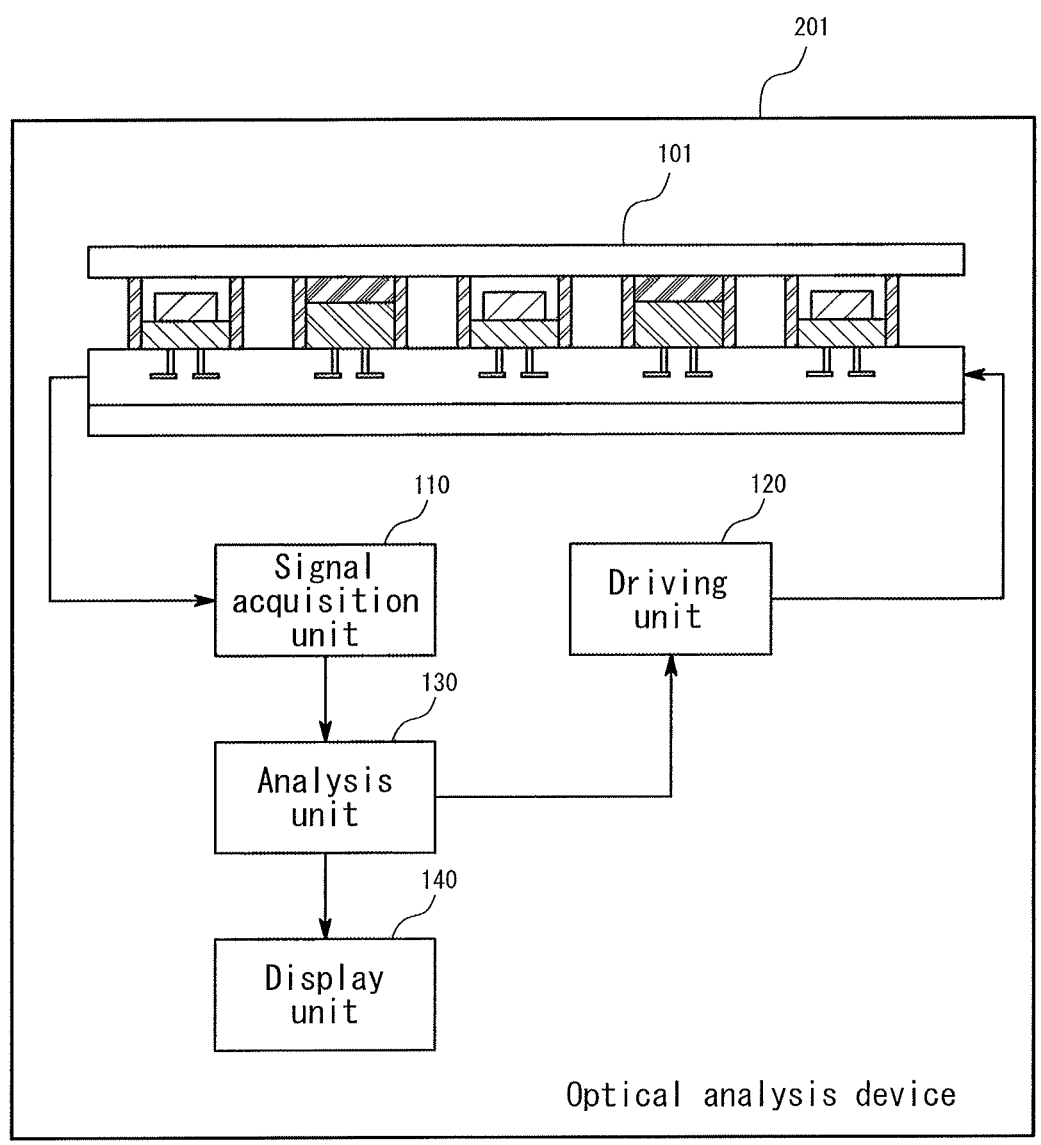
FIG. 8 is a block diagram schematically showing a configuration of an optical analysis device according to Embodiment 2 of the present invention.

Next, an optical analysis device according to Embodiment 2 will be described with reference to FIG. 8. FIG. 8 is a block diagram schematically showing the configuration of the optical analysis device according to Embodiment 2 of the present invention.

As shown in FIG. 8, similarly to the optical analysis device 200 of Embodiment 1 shown in FIG. 4, the optical analysis device 201 is a device that analyzes a specific component included in an analysis target 60. However, the optical analysis device 201 includes the optical unit 101 shown in FIGS. 5 to 7, instead of the optical unit 100 shown in FIGS. 1 to 3.

Note that the configuration of the optical analysis device 201 is similar to the optical analysis device 200 in Embodiment 1, except for the optical unit. Therefore, the optical analysis device 201 also includes a signal acquisition unit 110, a driving unit 120, an analysis unit 130, and a display unit 140. Since the functions of the signal acquisition unit 110, the driving unit 120, the analysis unit 130, and the display unit 140 are similar to those in Embodiment 1, description thereof is omitted in Embodiment 2.

Also, similarly to Embodiment 1, the signal acquisition unit 110, the driving unit 120, and the analysis unit 130 can be realized by an IC (Integrated Circuit) chip in Embodiment 2 as well. In this case, since the IC chips and the liquid crystal display panel functioning as the display unit 140 can be mounted on the mounting substrate 30 of the optical unit 101, it is possible to facilitate a further reduction in the size of the optical analysis device 201.

In Embodiment 2, a peak wavelength of light emitted from the light-emitting element 11 can be changed for every one or two or more light-emitting portions 10. Also, in accordance with this, the set wavelength of the optical filter 23 can be changed for every one or two or more light-receiving portions 20. In the case of such a mode, since the analysis unit 130 of the optical analysis device 201 can acquire the spectrum of the analysis target 60, it is possible to analyze a plurality of components included in the analysis target 60.

Embodiment 3

Figure 9:
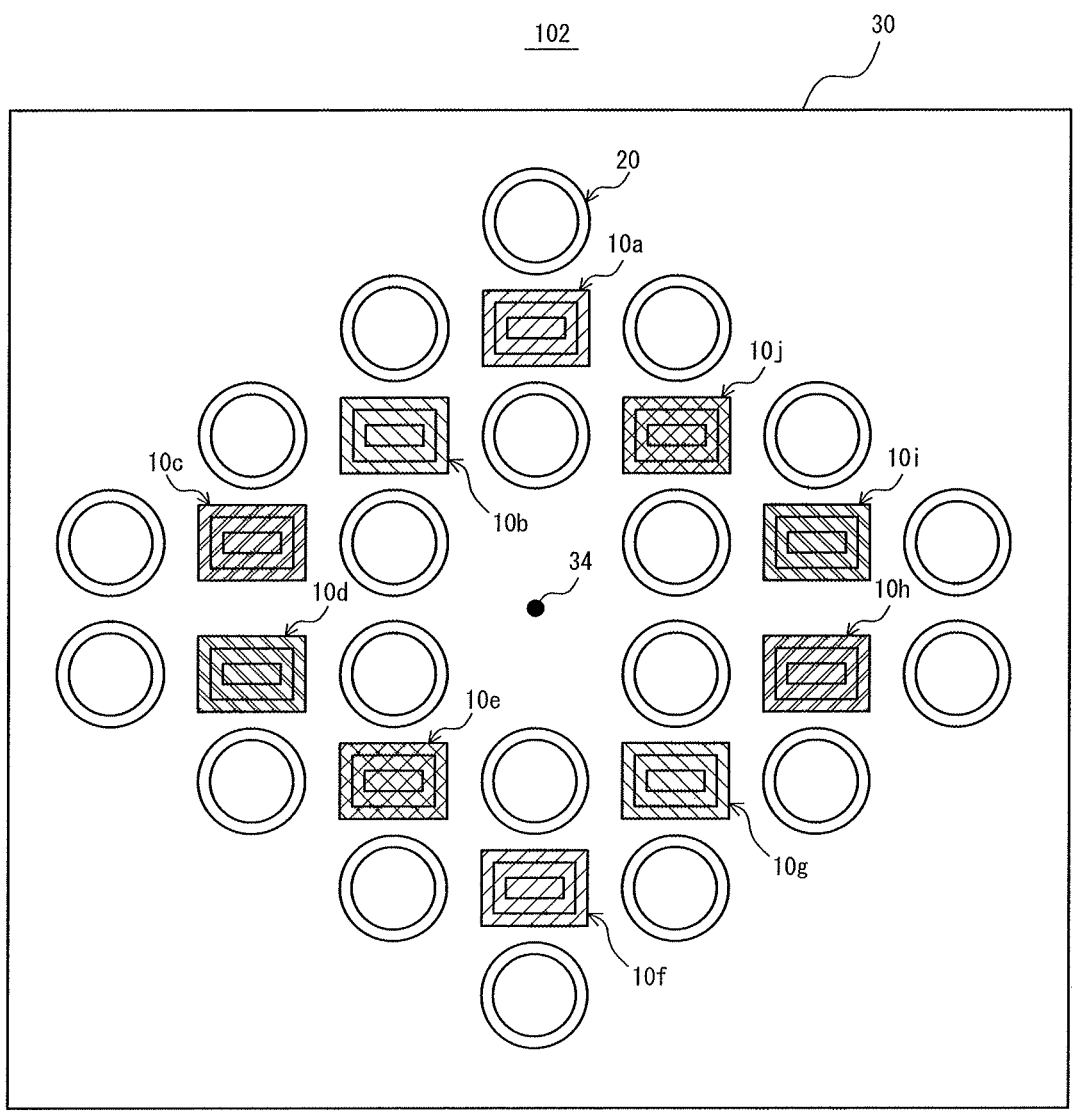
FIG. 9 is a plan view schematically showing a configuration of an optical unit according to Embodiment 3 of the present invention.

Next, an optical unit and an optical analysis device according to Embodiment 3 of the present invention will be described with reference to FIG. 9. FIG. 9 is a plan view schematically showing the configuration of the optical unit according to Embodiment 3 of the present invention.

An optical unit 102 of Embodiment 3 shown in FIG. 9 is configured similarly to the optical unit 101 of Embodiment 2, except that the light-emitting portions and the light-receiving portions are arranged differently. Hereinafter, Embodiment 3 will be described, focusing on the differences from Embodiment 2.

As shown in FIG. 9, in Embodiment 3, a plurality of light-emitting portions 10a to 10j are mounted on a mounting substrate 30 so as to respectively surround an arbitrary point 34 on the mounting substrate 30. This is because light can be emitted and received over a wide range of the analysis target (see FIG. 7)

Also, in Embodiment 3, the plurality of light-emitting portions 10a to 10j are constituted by a plurality of groups having mutually different peak wavelengths of light that is emitted therefrom, and each group has two light-emitting portions having the same peak wavelength.

Specifically, in the example of FIG. 9, the light-emitting portions 10a and 10f, the light-emitting portions 10b and 10g, the light-emitting portions 10c and 10h, the light-emitting portions 10d and 10i, and the light-emitting portions 10e and 10j respectively constitute a group. Note that the light-emitting portions belonging to the same group are hatched in the same manner in FIG. 9.

Furthermore, as shown in FIG. 9, the two light-emitting portions belonging to the same group are mounted at positions opposite each other across the arbitrary point 34. Note that although the two light-emitting portions belonging to the same group are mounted such that the distance from the arbitrary point 34 is mutually the same in the example of FIG. 9, Embodiment 3 is not limited to this example.

In this manner, with Embodiment 3, the optical unit 102 can emit light having different peak wavelengths. Accordingly, since the spectrum of the analysis target can be acquired by using the optical unit 102, a plurality of components included in the analysis target can be analyzed. Since two separate areas are irradiated with light having the same peak wavelength, an improvement in analysis accuracy in the optical analysis device (note shown) that uses the optical unit 102 can also be achieved.

Note that the optical analysis device of Embodiment 3 is configured similarly to the optical analysis device 200 (see FIG. 4) of Embodiment 1 and the optical analysis device 201 (see FIG. 8) of Embodiment 2, except that the optical unit 102 is used as the optical unit. Therefore, description of the optical analysis device of Embodiment 3 is omitted.

Embodiment 4

Figure 10:
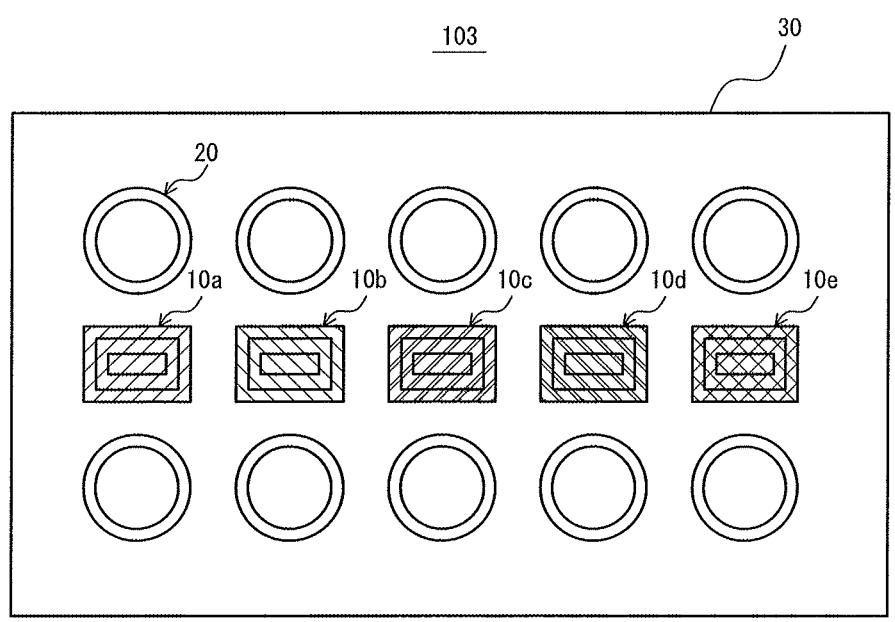
FIG. 10 is a plan view schematically showing a configuration of an optical unit according to Embodiment 4 of the present invention.

Next, an optical unit and an optical analysis device according to Embodiment 4 of the present invention will be described with reference to FIG. 10. FIG. 10 is a plan view schematically showing the configuration of the optical unit according to Embodiment 4 of the present invention.

An optical unit 103 of Embodiment 4 shown in FIG. 10 is configured similarly to the optical unit 101 of Embodiment 2, except that the light-emitting portions and the light-receiving portions are arranged differently. Hereinafter, Embodiment 4 will be described, focusing on the differences from Embodiment 2.

As shown in FIG. 10, in Embodiment 4, a plurality of light-emitting portions 10a to 10e are mounted on a mounting substrate 30 in a state in which the plurality of light-emitting portions are arranged linearly. This is because light can be emitted and received over a wide range of the analysis target (see FIG. 7), and a reduction in the manufacturing cost of the optical unit 103 can be achieved by facilitating mounting of the light-emitting portions on the mounting substrate 30. Note that each light-emitting portion is hatched differently in FIG. 10.

Also, peak wavelengths of light that is emitted from the light-emitting portions 10a to 10e are different from each other in Embodiment 4 as well. Accordingly, since the spectrum of the analysis target can be acquired even in the case where the optical unit 103 is used, a plurality of components included in the analysis target can be analyzed.

Note that the optical analysis device of Embodiment 4 is configured similarly to the optical analysis device 200 (see FIG. 4) of Embodiment 1 and the optical analysis device 201 (see FIG. 8) of Embodiment 2, except that the optical unit 103 is used as the optical unit Therefore, description of the optical analysis device of Embodiment 4 is also omitted.

Although the above-described embodiments can be partially or wholly represented by supplementary note 1 to supplementary note 20 described below, the present invention is not limited to the following description.

Supplementary Note 1

An optical unit comprising:
a light-emitting portion that irradiates an analysis target with light;
a plurality of light-receiving portions that receive light that has been reflected or diffused by the analysis target;
a mounting substrate on which the light-emitting portion and the plurality of light-receiving portions are mounted; and a plate-shaped member having optical transparency, wherein the plate-shaped member is arranged so as to cover the light-emitting portion and the plurality of light-receiving portions that are mounted on the mounting substrate, and positions of the light-emitting portion, the light-receiving portions, and the plate-shaped member are respectively set such that, in a case where the analysis target is in contact with the plate-shaped member, light emitted from the light-emitting portion is incident on two or more of the light-receiving portions after being reflected or diffused by the analysis target.

Supplementary Note 2

The optical unit according to supplementary note 1, comprising:

a plurality of the light-emitting portions, the plurality of light-emitting portions being mounted on the mounting substrate, wherein positions of the light-emitting portions, the light-receiving portions, and the plate-shaped member are respectively set such that, in a case where the analysis target is in contact with the plate-shaped member, light emitted from each of the light-emitting portions is incident on two or more of the light-receiving portions after being reflected or diffused by the analysis target.

Supplementary Note 3

The optical unit according to supplementary note 1, wherein the light-emitting portion includes a light-emitting element arranged so that an emission surface faces the plate-shaped member, and a light-blocking wall provided so as to cover the emission surface, and the light-receiving portions each includes a light-receiving element arranged so that a light-receiving surface faces the plate-shaped member, and a light-blocking wall provided so as to surround the light-receiving surface.

Supplementary Note 4

The optical unit according to supplementary note 1, wherein the light-emitting portion includes, between the light-emitting element and the mounting substrate, a heat transmission member for transmitting heat generated in the light-emitting element to the mounting substrate.

Supplementary Note 5

The optical unit according to supplementary note 1, wherein a height of each of the light-blocking wall of the light-emitting portion and the light-blocking wall of each light-receiving portion is set so as to match a distance between the plate-shaped member and the mounting substrate.

Supplementary Note 6

The optical unit according to supplementary note 1, further comprising:

a cooling element, wherein the cooling element is arranged so as to be in contact with a surface of the mounting substrate on which the light-emitting portions and the plurality of light-receiving portions are not mounted.

Supplementary Note 7

The optical unit according to supplementary note 1, wherein each of the plurality of light-receiving portions includes, on an incident side of the light-receiving surface, an optical filter that transmits only light having a set wavelength.

Supplementary Note 8

The optical unit according to supplementary note 2, wherein the plurality of light-emitting portions are mounted on the mounting substrate so as to respectively surround an arbitrary point on the mounting substrate.

Supplementary Note 9

The optical unit according to supplementary note 8, wherein the plurality of light-emitting portions are constituted by a plurality of groups having mutually different peak wavelengths of light that is emitted, and each of the plurality of groups has two light-emitting portions having the same peak wavelength, and the two light-emitting portions belonging to the same group are mounted at positions opposite each other across the arbitrary point.

Supplementary Note 10

The optical unit according to supplementary note 2, wherein the plurality of light-emitting portions are mounted on the mounting substrate in a state in which the plurality of light-emitting portions are arranged linearly.

Supplementary Note 11

An optical analysis device for analyzing a specific component included in an analysis target, the device comprising:

an optical unit including a light-emitting portion that irradiates the analysis target with light, a plurality of light-receiving portions that receive light that has been reflected or diffused by the analysis target, a mounting substrate on which the light-emitting portion and the plurality of light-receiving portions are mounted, and a plate-shaped member having optical transparency, wherein the plate-shaped member is arranged so as to cover the light-emitting portion and the plurality of light-receiving portions that are mounted on the mounting substrate, and positions of the light-emitting portion, the light-receiving portions, and the plate-shaped member are respectively set such that, in a case where the analysis target is in contact with the plate-shaped member, light emitted from the light-emitting portion is incident on two or more of the light-receiving portions after being reflected or diffused by the analysis target.

Supplementary Note 12

The optical analysis device according to supplementary note 11, comprising:

a plurality of the light-emitting portions, the plurality of light-emitting portions being mounted on the mounting substrate, wherein positions of the light-emitting portions, the light-receiving portions, and the plate-shaped member are respectively set such that, in a case where the analysis target is in contact with the plate-shaped member, light emitted from each of the light-emitting portions is incident on two or more of the light-receiving portions after being reflected or diffused by the analysis target.

Supplementary Note 13

The optical analysis device according to supplementary note 11, wherein the light-emitting portion includes a light-emitting element arranged so that an emission surface faces the plate-shaped member, and a light-blocking wall provided so as to cover the emission surface, and the light-receiving portions each includes a light-receiving element arranged so that a light-receiving surface faces the plate-shaped member, and a light-blocking wall provided so as to surround the light-receiving surface.

Supplementary Note 14

The optical analysis device according to supplementary note 11, wherein the light-emitting portion includes, between the light-emitting element and the mounting substrate, a heat transmission member for transmitting heat generated in the light-emitting element to the mounting substrate.

Supplementary Note 15

The optical analysis device according to supplementary note 11, wherein a height of each of the light-blocking wall of the light-emitting portion and the light-blocking wall of each light-receiving portion is set so as to match a distance between the plate-shaped member and the mounting substrate.

Supplementary Note 16

The optical analysis device according to supplementary note 11, further comprising:

a cooling element, wherein the cooling element is arranged so as to be in contact with a surface of the mounting substrate on which the light-emitting portions and the plurality of light-receiving portions are not mounted.

Supplementary Note 17

The optical analysis device according to supplementary note 11, wherein each of the plurality of light-receiving portions includes, on an incident side of the light-receiving surface, an optical filter that transmits only light having a set wavelength.

Supplementary Note 18

The optical analysis device according to supplementary note 12, wherein the plurality of light-emitting portions are mounted on the mounting substrate so as to respectively surround an arbitrary point on the mounting substrate.

Supplementary Note 19

The optical analysis device according to supplementary note 18, wherein the plurality of light-emitting portions are constituted by a plurality of groups having mutually different peak wavelengths of light that is emitted, and each of the plurality of groups has two light-emitting portions having the same peak wavelength, and the two light-emitting portions belonging to the same group are mounted at positions opposite each other across the arbitrary point.

Supplementary Note 20

The optical analysis device according to supplementary note 12, wherein the plurality of light-emitting portions are mounted on the mounting substrate in a state in which the plurality of light-emitting portions are arranged linearly.

Although the present invention has been described with reference to embodiments, the present invention is not limited to the above-described embodiments. The configuration and details of the present invention can be modified in various ways that will be evident to a person skilled in the art within the scope of the present invention.

This application is based upon and claims the benefit of Japanese Patent Application No. 2013-122434, filed Jun. 11, 2013, the disclosure of which is incorporated herein in its entirety by reference.

INDUSTRIAL APPLICABILITY

As described above, according to the present invention, a reduction in the size of an optical analysis device can be achieved. Also, the present invention is useful for various types of analysis targeting fruits, vegetables, other foodstuffs, chemical substances, and living bodies.

REFERENCE SIGNS LIST 10, 10a to 10j Light-emitting portion
11 Light-emitting element
11a Emission surface
12 Light-blocking wall
13 Heat transmission member
20 Light-receiving portion
21 Light-receiving element
21a Light-receiving surface
22 Light-blocking wall
23 Optical filter.
30 Mounting substrate
31 Conduction channel
32 Wiring
33 Heat conduction channel
40 Plate-shaped member
50 Cooling element
60 Analysis target
100 Optical unit (Embodiment 1)
101 Optical unit (Embodiment 2)
102 Optical unit (Embodiment 3)
103 Optical unit (Embodiment 4)
110 Signal acquisition unit
120 Driving unit
130 Analysis unit
140 Display unit
200 Optical analysis device (Embodiment 1)
201 Optical analysis device (Embodiment 2)

The invention claimed is:

1. An optical unit comprising:

a light emitter that irradiates an analysis target with light;

a plurality of light receivers that receive light that has been reflected or diffused by the analysis target;

a mounting substrate on which the light emitter and the plurality of light receivers are mounted; and a plate-shaped member having optical transparency, wherein the plate-shaped member is arranged so as to cover the light emitter and the plurality of light receivers that are mounted on the mounting substrate, and positions of the light emitter, the light receivers, and the plate-shaped member are respectively set such that, in a case where the analysis target is in contact with the plate-shaped member, light emitted from the light emitter is incident on two or more of the light receivers after being reflected or diffused by the analysis target, wherein the optical unit further comprises a cooler, the light emitter comprises, between a light-emitting diode and the mounting substrate, a heat transmitter for transmitting heat generated in the light-emitting diode to the mounting substrate, the cooler is arranged in contact with a surface of the mounting substrate on which the light emitter and each light receiver are not mounted, and the mounting substrate comprises:

a conduction channel that is connected to the light-emitting diode and a light receiving photodiode of each light receiver;

a wiring that is formed inside the mounting substrate and is connected to the conduction channel; and a heat channel that connects the wiring and the cooler.

2. The optical unit according to claim 1, comprising:

a plurality of the light emitters, the plurality of light emitters being mounted on the mounting substrate, wherein positions of the light emitters, the light receivers, and the plate-shaped member are respectively set such that, in a case where the analysis target is in contact with the plate-shaped member, light emitted from each light emitter of the plurality of light emitters is incident on two or more of the light receivers after being reflected or diffused by the analysis target.

3. The optical unit according to claim 2, wherein the plurality of light emitters are mounted on the mounting substrate so as to respectively surround an arbitrary point on the mounting substrate.

4. The optical unit according to claim 3,
wherein the plurality of light emitters are constituted by a plurality of groups having mutually different peak wavelengths of light that is emitted, and each of the plurality of groups has two light emitters having the same peak wavelength, and
the two light emitters belonging to the same group are mounted at positions opposite each other across the arbitrary point.

5. The optical unit according to claim 2, wherein the plurality of light emitters are mounted on the mounting substrate in a state in which the plurality of light emitters are arranged linearly.

6. The optical unit according to claim 2,
wherein each light emitter of the plurality of light emitters includes a light-emitting diode arranged so that an emission surface faces the plate-shaped member, and a light-blocking wall provided so as to cover the emission surface, and
the light receivers each include a light-receiving photodiode arranged so that a light-receiving surface faces the plate-shaped member, and a light-blocking wall provided so as to surround the light-receiving surface.

7. The optical unit according to claim 6, wherein a height of each light-blocking wall of each light emitter of the plurality of light emitters and each light-blocking wall of each light receiver of the plurality of light receivers is set so as to match a distance between the plate-shaped member and the mounting substrate.

8. The optical unit according to claim 1, wherein each of the plurality of light receivers includes, on an incident side of the light-receiving surface, an optical filter that transmits only light having a set wavelength.

9. An optical analysis device for analyzing a specific component included in an analysis target, the device comprising:
an interface;
an optical unit coupled to the interface and including a light emitter that irradiates the analysis target with light, a plurality of light receivers that receive light that has been reflected or diffused by the analysis target, a mounting substrate on which the light emitter and the plurality of light receivers are mounted, and a plate-shaped member having optical transparency,
wherein the plate-shaped member is arranged so as to cover the light emitter and the plurality of light receivers that are mounted on the mounting substrate, and
positions of the light emitter, the light receivers, and the plate-shaped member are respectively set such that, in a case where the analysis target is in contact with the plate-shaped member, light emitted from the light emitter is incident on two or more of the light receivers after being reflected or diffused by the analysis target,
wherein the optical unit further comprises a cooler,
the light emitter comprises, between a light-emitting diode and the mounting substrate, a heat transmitter for transmitting heat generated in the light-emitting diode to the mounting substrate,
the cooler is arranged in contact with a surface of the mounting substrate on which the light emitter and each light receiver are not mounted, and
the mounting substrate comprises:
a conduction channel that is connected to the light-emitting diode and a light receiving photodiode of each light receiver;
a wiring that is formed inside the mounting substrate and is connected to the conduction channel; and
a heat channel that connects the wiring and the cooler.

10. The optical analysis device according to claim 9, comprising:
a plurality of the light emitters, the plurality of light emitters being mounted on the mounting substrate,
wherein positions of the light emitters, the light receivers, and the plate-shaped member are respectively set such that, in a case where the analysis target is in contact with the plate-shaped member, light emitted from each of the light emitters is incident on two or more of the light receivers after being reflected or diffused by the analysis target.

11. The optical analysis device according to claim 10, wherein the plurality of light emitters are mounted on the mounting substrate so as to respectively surround an arbitrary point on the mounting substrate.

12. The optical analysis device according to claim 11,
wherein the plurality of light emitters are constituted by a plurality of groups having mutually different peak wavelengths of light that is emitted, and each of the plurality of groups has two light emitters having the same peak wavelength, and
the two light emitters belonging to the same group are mounted at positions opposite each other across the arbitrary point.

13. The optical analysis device according to claim 10, wherein the plurality of light emitters are mounted on the mounting substrate in a state in which the plurality of light emitters are arranged linearly.

14. The optical analysis device according to claim 10,
wherein each light emitter of the plurality of light emitters includes a light-emitting diode arranged so that an emission surface faces the plate-shaped member, and a light-blocking wall provided so as to cover the emission surface, and
the light receivers each include a light-receiving photodiode arranged so that a light-receiving surface faces the plate-shaped member, and a light-blocking wall provided so as to surround the light-receiving surface.

15. The optical analysis device according to claim 14, wherein a height of each light-blocking wall of each light emitter of the plurality of light emitters and each light-blocking wall of each light receiver of the plurality of light receivers is set so as to match a distance between the plate-shaped member and the mounting substrate.

16. The optical analysis device according to claim 9, wherein each of the plurality of light receivers includes, on an incident side of the light-receiving surface, an optical filter that transmits only light having a set wavelength.

* * * * *